US012805874B2

(12) United States Patent
Joyce et al.

(10) Patent No.: US 12,805,874 B2

(45) Date of Patent: Nov. 24, 2026

(54) CUT OPTIMIZATION FOR EXCESSIVE TISSUE CONDITIONS

(71) Applicant: Covidien LP, Mansfield, MA (US)

(72) Inventors: Steven H. Joyce, Durham, CT (US); David E. Valentine, Hamden, CT (US); Patrick Mozdzierz, Glastonbury, CT (US); Charles R. Kollar, Washington, DC (US); Haley Strassner, New Haven, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 19/244,006

(22) Filed: Jun. 20, 2025

(65) Prior Publication Data

US 2025/0312045 A1 Oct. 9, 2025

Related U.S. Application Data

(63) Continuation of application No. 18/585,215, filed on Feb. 23, 2024, now Pat. No. 12,357,313, which is a continuation of application No. 17/120,659, filed on Dec. 14, 2020, now Pat. No. 11,911,038.

(60) Provisional application No. 62/960,202, filed on Jan. 13, 2020.

(51) Int. Cl.

| | |
|---|---|
| ***A61B 17/072*** | (2006.01) |
| ***A61B 17/115*** | (2006.01) |
| ***A61B 17/32*** | (2006.01) |

(52) U.S. Cl.

CPC .......... *A61B 17/1155* (2013.01); *A61B 17/32* (2013.01)

(58) Field of Classification Search

CPC ............................ A61B 17/115; A61B 17/072

See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |

(Continued)

FOREIGN PATENT DOCUMENTS

| | | | |
|---|---|---|---|
| CA | 908529 | A | 8/1972 |
| CA | 2805365 | A1 | 8/2013 |

(Continued)

OTHER PUBLICATIONS

Examiner Interview Summary Record received for U.S. Appl. No. 18/585,215, mailed on Oct. 12, 2023, 3 pages.

(Continued)

*Primary Examiner* — Gloria R Weeks

(57) ABSTRACT

A method of operating a surgical stapler includes advancing a knife assembly at a first velocity until a predetermined force is detected, advancing the knife assembly at a second velocity when the predetermined force is detected, the second velocity being less than the first velocity, and continuing to advance the knife assembly at the second velocity until the knife assembly travels a cutting stroke distance.

14 Claims, 3 Drawing Sheets

(56) References Cited

U.S. PATENT DOCUMENTS

| | | | |
|---|---|---|---|
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |
| 4,473,077 | A | 9/1984 | Noiles et al. |
| 4,476,863 | A | 10/1984 | Kanshin et al. |
| 4,485,817 | A | 12/1984 | Swiggett |
| 4,488,523 | A | 12/1984 | Shichman |
| 4,505,272 | A | 3/1985 | Utyamyshev et al. |
| 4,505,414 | A | 3/1985 | Filipi |
| 4,520,817 | A | 6/1985 | Green |
| 4,550,870 | A | 11/1985 | Krumme et al. |
| 4,573,468 | A | 3/1986 | Conta et al. |
| 4,576,167 | A | 3/1986 | Noiles |
| 4,592,354 | A | 6/1986 | Rothfuss |
| 4,603,693 | A | 8/1986 | Conta et al. |
| 4,606,343 | A | 8/1986 | Conta et al. |
| 4,632,290 | A | 12/1986 | Green et al. |
| 4,646,745 | A | 3/1987 | Noiles |
| 4,665,917 | A | 5/1987 | Clanton et al. |
| 4,667,673 | A | 5/1987 | Li |
| 4,671,445 | A | 6/1987 | Barker et al. |
| 4,700,703 | A | 10/1987 | Resnick et al. |
| 4,703,887 | A | 11/1987 | Clanton et al. |
| 4,708,141 | A | 11/1987 | Inoue et al. |
| 4,717,063 | A | 1/1988 | Ebihara |
| 4,752,024 | A | 6/1988 | Green et al. |
| 4,754,909 | A | 7/1988 | Barker et al. |
| 4,776,506 | A | 10/1988 | Green |
| 4,817,847 | A | 4/1989 | Redtenbacher et al. |
| 4,873,977 | A | 10/1989 | Avant et al. |
| 4,893,662 | A | 1/1990 | Gervasi |
| 4,903,697 | A | 2/1990 | Resnick et al. |
| 4,907,591 | A | 3/1990 | Vasconcellos et al. |
| 4,917,114 | A | 4/1990 | Green et al. |
| 4,957,499 | A | 9/1990 | Lipatov et al. |
| 4,962,877 | A | 10/1990 | Hervas |
| 5,005,749 | A | 4/1991 | Aranyi |
| 5,042,707 | A | 8/1991 | Taheri |
| 5,047,039 | A | 9/1991 | Avant et al. |
| 5,104,025 | A | 4/1992 | Main et al. |
| 5,119,983 | A | 6/1992 | Green et al. |
| 5,122,156 | A | 6/1992 | Granger et al. |
| 5,139,513 | A | 8/1992 | Segato |
| 5,158,222 | A | 10/1992 | Green et al. |
| 5,188,638 | A | 2/1993 | Tzakis |
| 5,193,731 | A | 3/1993 | Aranyi |
| 5,197,648 | A | 3/1993 | Gingold |
| 5,197,649 | A | 3/1993 | Bessler et al. |
| 5,205,459 | A | 4/1993 | Brinkerhoff et al. |
| 5,221,036 | A | 6/1993 | Takase |
| 5,222,963 | A | 6/1993 | Brinkerhoff et al. |
| 5,253,793 | A | 10/1993 | Green et al. |
| 5,261,920 | A | 11/1993 | Main et al. |
| 5,271,543 | A | 12/1993 | Grant et al. |
| 5,271,544 | A | 12/1993 | Fox et al. |
| 5,275,322 | A | 1/1994 | Brinkerhoff et al. |
| 5,282,810 | A | 2/1994 | Allen et al. |
| 5,285,944 | A | 2/1994 | Green et al. |
| 5,285,945 | A | 2/1994 | Brinkerhoff et al. |
| 5,292,053 | A | 3/1994 | Bilotti et al. |
| 5,309,927 | A | 5/1994 | Welch |
| 5,312,024 | A | 5/1994 | Grant et al. |
| 5,314,435 | A | 5/1994 | Green et al. |
| 5,314,436 | A | 5/1994 | Wilk |
| 5,330,486 | A | 7/1994 | Wilk |
| 5,333,773 | A | 8/1994 | Main et al. |
| 5,344,059 | A | 9/1994 | Green et al. |
| 5,346,115 | A | 9/1994 | Perouse et al. |
| 5,348,259 | A | 9/1994 | Blanco et al. |
| 5,350,104 | A | 9/1994 | Main et al. |
| 5,355,897 | A | 10/1994 | Pietrafitta et al. |
| 5,360,154 | A | 11/1994 | Green |
| 5,368,215 | A | 11/1994 | Green et al. |
| 5,392,979 | A | 2/1995 | Green et al. |
| 5,395,030 | A | 3/1995 | Kuramoto et al. |
| 5,403,333 | A | 4/1995 | Kaster et al. |
| 5,404,870 | A | 4/1995 | Brinkerhoff et al. |
| 5,411,508 | A | 5/1995 | Bessler et al. |
| 5,425,738 | A | 6/1995 | Gustafson et al. |
| 5,433,721 | A | 7/1995 | Hooven et al. |
| 5,437,684 | A | 8/1995 | Calabrese et al. |
| 5,439,156 | A | 8/1995 | Grant et al. |
| 5,443,198 | A | 8/1995 | Viola et al. |
| 5,447,514 | A | 9/1995 | Gerry et al. |
| 5,454,825 | A | 10/1995 | Van Leeuwen et al. |
| 5,464,144 | A | 11/1995 | Guy et al. |
| 5,464,415 | A | 11/1995 | Chen |
| 5,470,006 | A | 11/1995 | Rodak |
| 5,474,223 | A | 12/1995 | Viola et al. |
| 5,497,934 | A | 3/1996 | Brady et al. |
| 5,503,635 | A | 4/1996 | Sauer et al. |
| 5,522,534 | A | 6/1996 | Viola et al. |
| 5,533,661 | A | 7/1996 | Main et al. |
| 5,588,579 | A | 12/1996 | Schnut et al. |
| 5,609,285 | A | 3/1997 | Grant et al. |
| 5,626,591 | A | 5/1997 | Koeckerling et al. |
| 5,632,433 | A | 5/1997 | Grant et al. |
| 5,639,008 | A | 6/1997 | Gallagher et al. |
| 5,641,111 | A | 6/1997 | Ahrens et al. |
| 5,658,300 | A | 8/1997 | Bito et al. |
| 5,669,918 | A | 9/1997 | Balazs et al. |
| 5,685,474 | A | 11/1997 | Seeber |
| 5,709,335 | A | 1/1998 | Heck |
| 5,715,987 | A | 2/1998 | Kelley et al. |
| 5,718,360 | A | 2/1998 | Green et al. |
| 5,720,755 | A | 2/1998 | Dakov |
| 5,732,872 | A | 3/1998 | Bolduc et al. |
| 5,749,896 | A | 5/1998 | Cook |
| 5,758,814 | A | 6/1998 | Gallagher et al. |
| 5,799,857 | A | 9/1998 | Robertson et al. |
| 5,814,055 | A | 9/1998 | Knodel et al. |
| 5,833,698 | A | 11/1998 | Hinchliffe et al. |
| 5,836,503 | A | 11/1998 | Ehrenfels et al. |
| 5,839,639 | A | 11/1998 | Sauer et al. |
| 5,855,312 | A | 1/1999 | Toledano |
| 5,860,581 | A | 1/1999 | Robertson et al. |
| 5,868,760 | A | 2/1999 | McGuckin, Jr. |
| 5,881,943 | A | 3/1999 | Heck et al. |
| 5,915,616 | A | 6/1999 | Viola et al. |
| 5,947,363 | A | 9/1999 | Bolduc et al. |
| 5,951,576 | A | 9/1999 | Wakabayashi |
| 5,957,363 | A | 9/1999 | Heck |
| 5,993,468 | A | 11/1999 | Rygaard |
| 6,024,748 | A | 2/2000 | Manzo et al. |
| 6,050,472 | A | 4/2000 | Shibata |
| 6,053,390 | A | 4/2000 | Green et al. |
| 6,068,636 | A | 5/2000 | Chen |
| 6,083,241 | A | 7/2000 | Longo et al. |
| 6,102,271 | A | 8/2000 | Longo et al. |
| 6,117,148 | A | 9/2000 | Ravo et al. |
| 6,119,913 | A | 9/2000 | Adams et al. |
| 6,126,058 | A | 10/2000 | Adams et al. |
| 6,142,933 | A | 11/2000 | Longo et al. |
| 6,149,667 | A | 11/2000 | Hovland et al. |
| 6,176,413 | B1 | 1/2001 | Heck et al. |
| 6,179,195 | B1 | 1/2001 | Adams et al. |
| 6,193,129 | B1 | 2/2001 | Bittner et al. |
| 6,203,553 | B1 | 3/2001 | Robertson et al. |
| 6,209,773 | B1 | 4/2001 | Bolduc et al. |
| 6,241,140 | B1 | 6/2001 | Adams et al. |
| 6,253,984 | B1 | 7/2001 | Heck et al. |
| 6,258,107 | B1 | 7/2001 | Balazs et al. |
| 6,264,086 | B1 | 7/2001 | McGuckin, Jr. |
| 6,269,997 | B1 | 8/2001 | Balazs et al. |
| 6,273,897 | B1 | 8/2001 | Dalessandro et al. |
| 6,279,809 | B1 | 8/2001 | Nicolo |
| 6,302,311 | B1 | 10/2001 | Adams et al. |
| 6,338,737 | B1 | 1/2002 | Toledano |
| 6,343,731 | B1 | 2/2002 | Adams et al. |
| 6,387,105 | B1 | 5/2002 | Gifford, III et al. |
| 6,398,795 | B1 | 6/2002 | McAlister et al. |
| 6,402,008 | B1 | 6/2002 | Lucas |
| 6,439,446 | B1 | 8/2002 | Perry et al. |

(56) References Cited

U.S. PATENT DOCUMENTS

| | | | |
|---|---|---|---|
| 6,443,973 | B1 | 9/2002 | Whitman |
| 6,450,390 | B2 | 9/2002 | Heck et al. |
| 6,478,210 | B2 | 11/2002 | Adams et al. |
| 6,488,197 | B1 | 12/2002 | Whitman |
| 6,491,201 | B1 | 12/2002 | Whitman |
| 6,494,877 | B2 | 12/2002 | Odell et al. |
| 6,503,259 | B2 | 1/2003 | Huxel et al. |
| 6,517,566 | B1 | 2/2003 | Hovland et al. |
| 6,520,398 | B2 | 2/2003 | Nicolo |
| 6,533,157 | B1 | 3/2003 | Whitman |
| 6,551,334 | B2 | 4/2003 | Blatter et al. |
| 6,578,751 | B2 | 6/2003 | Hartwick |
| 6,585,144 | B2 | 7/2003 | Adams et al. |
| 6,588,643 | B2 | 7/2003 | Bolduc et al. |
| 6,592,596 | B1 | 7/2003 | Geitz |
| 6,601,749 | B2 | 8/2003 | Sullivan et al. |
| 6,605,078 | B2 | 8/2003 | Adams |
| 6,605,098 | B2 | 8/2003 | Nobis et al. |
| 6,626,921 | B2 | 9/2003 | Blatter et al. |
| 6,629,630 | B2 | 10/2003 | Adams |
| 6,631,837 | B1 | 10/2003 | Heck |
| 6,632,227 | B2 | 10/2003 | Adams |
| 6,632,237 | B2 | 10/2003 | Ben-David et al. |
| 6,652,542 | B2 | 11/2003 | Blatter et al. |
| 6,659,327 | B2 | 12/2003 | Heck et al. |
| 6,676,671 | B2 | 1/2004 | Robertson et al. |
| 6,681,979 | B2 | 1/2004 | Whitman |
| 6,685,079 | B2 | 2/2004 | Sharma et al. |
| 6,695,198 | B2 | 2/2004 | Adams et al. |
| 6,695,199 | B2 | 2/2004 | Whitman |
| 6,698,643 | B2 | 3/2004 | Whitman |
| 6,716,222 | B2 | 4/2004 | McAlister et al. |
| 6,716,233 | B1 | 4/2004 | Whitman |
| 6,726,697 | B2 | 4/2004 | Nicholas et al. |
| 6,742,692 | B2 | 6/2004 | Hartwick |
| 6,743,244 | B2 | 6/2004 | Blatter et al. |
| 6,763,993 | B2 | 7/2004 | Bolduc et al. |
| 6,769,590 | B2 | 8/2004 | Vresh et al. |
| 6,769,594 | B2 | 8/2004 | Orban, III |
| 6,820,791 | B2 | 11/2004 | Adams |
| 6,821,282 | B2 | 11/2004 | Perry et al. |
| 6,827,246 | B2 | 12/2004 | Sullivan et al. |
| 6,840,423 | B2 | 1/2005 | Adams et al. |
| 6,843,403 | B2 | 1/2005 | Whitman |
| 6,846,308 | B2 | 1/2005 | Whitman et al. |
| 6,852,122 | B2 | 2/2005 | Rush |
| 6,866,178 | B2 | 3/2005 | Adams et al. |
| 6,872,214 | B2 | 3/2005 | Sonnenschein et al. |
| 6,874,669 | B2 | 4/2005 | Adams et al. |
| 6,884,250 | B2 | 4/2005 | Monassevitch et al. |
| 6,905,504 | B1 | 6/2005 | Vargas |
| 6,938,814 | B2 | 9/2005 | Sharma et al. |
| 6,942,675 | B1 | 9/2005 | Vargas |
| 6,945,444 | B2 | 9/2005 | Gresham et al. |
| 6,953,138 | B1 | 10/2005 | Dworak et al. |
| 6,957,758 | B2 | 10/2005 | Aranyi |
| 6,959,851 | B2 | 11/2005 | Heinrich |
| 6,978,922 | B2 | 12/2005 | Bilotti et al. |
| 6,981,941 | B2 | 1/2006 | Whitman et al. |
| 6,981,979 | B2 | 1/2006 | Nicolo |
| 7,032,798 | B2 | 4/2006 | Whitman et al. |
| 7,059,331 | B2 | 6/2006 | Adams et al. |
| 7,059,510 | B2 | 6/2006 | Orban, III |
| 7,077,856 | B2 | 7/2006 | Whitman |
| 7,080,769 | B2 | 7/2006 | Vresh et al. |
| 7,086,267 | B2 | 8/2006 | Dworak et al. |
| 7,114,642 | B2 | 10/2006 | Whitman |
| 7,118,528 | B1 | 10/2006 | Piskun |
| 7,122,044 | B2 | 10/2006 | Bolduc et al. |
| 7,128,748 | B2 | 10/2006 | Mooradian et al. |
| 7,141,055 | B2 | 11/2006 | Abrams et al. |
| 7,168,604 | B2 | 1/2007 | Milliman et al. |
| 7,179,267 | B2 | 2/2007 | Nolan et al. |
| 7,182,239 | B1 | 2/2007 | Myers |
| 7,195,142 | B2 | 3/2007 | Orban, III |
| 7,207,168 | B2 | 4/2007 | Doepker et al. |
| 7,220,237 | B2 | 5/2007 | Gannoe et al. |
| 7,234,624 | B2 | 6/2007 | Gresham et al. |
| 7,235,089 | B1 | 6/2007 | McGuckin, Jr. |
| RE39,841 | E | 9/2007 | Bilotti et al. |
| 7,285,125 | B2 | 10/2007 | Viola |
| 7,303,106 | B2 | 12/2007 | Milliman et al. |
| 7,303,107 | B2 | 12/2007 | Milliman et al. |
| 7,309,341 | B2 | 12/2007 | Ortiz et al. |
| 7,322,994 | B2 | 1/2008 | Nicholas et al. |
| 7,325,713 | B2 | 2/2008 | Aranyi |
| 7,334,718 | B2 | 2/2008 | McAlister et al. |
| 7,335,212 | B2 | 2/2008 | Edoga et al. |
| 7,364,060 | B2 | 4/2008 | Milliman |
| 7,398,908 | B2 | 7/2008 | Holsten et al. |
| 7,399,305 | B2 | 7/2008 | Csiky et al. |
| 7,401,721 | B2 | 7/2008 | Holsten et al. |
| 7,401,722 | B2 | 7/2008 | Hur |
| 7,407,075 | B2 | 8/2008 | Holsten et al. |
| 7,410,086 | B2 | 8/2008 | Ortiz et al. |
| 7,422,136 | B1 | 9/2008 | Marczyk |
| 7,422,137 | B2 | 9/2008 | Manzo |
| 7,422,138 | B2 | 9/2008 | Bilotti et al. |
| 7,431,191 | B2 | 10/2008 | Milliman |
| 7,438,718 | B2 | 10/2008 | Milliman et al. |
| 7,455,676 | B2 | 11/2008 | Holsten et al. |
| 7,455,682 | B2 | 11/2008 | Viola |
| 7,481,347 | B2 | 1/2009 | Roy |
| 7,494,038 | B2 | 2/2009 | Milliman |
| 7,506,791 | B2 | 3/2009 | Omaits et al. |
| 7,516,877 | B2 | 4/2009 | Aranyi |
| 7,527,185 | B2 | 5/2009 | Harari et al. |
| 7,537,602 | B2 | 5/2009 | Whitman |
| 7,540,839 | B2 | 6/2009 | Butler et al. |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,556,186 | B2 | 7/2009 | Milliman |
| 7,559,451 | B2 | 7/2009 | Sharma et al. |
| 7,585,306 | B2 | 9/2009 | Abbott et al. |
| 7,588,174 | B2 | 9/2009 | Holsten et al. |
| 7,600,663 | B2 | 10/2009 | Green |
| 7,611,038 | B2 | 11/2009 | Racenet et al. |
| 7,635,385 | B2 | 12/2009 | Milliman et al. |
| 7,669,747 | B2 | 3/2010 | Weisenburgh, II et al. |
| 7,686,201 | B2 | 3/2010 | Csiky |
| 7,694,864 | B2 | 4/2010 | Okada et al. |
| 7,699,204 | B2 | 4/2010 | Viola |
| 7,708,181 | B2 | 5/2010 | Cole et al. |
| 7,717,313 | B2 | 5/2010 | Criscuolo et al. |
| 7,721,932 | B2 | 5/2010 | Cole et al. |
| 7,726,539 | B2 | 6/2010 | Holsten et al. |
| 7,743,958 | B2 | 6/2010 | Orban, III |
| 7,744,627 | B2 | 6/2010 | Orban, III et al. |
| 7,770,776 | B2 | 8/2010 | Chen et al. |
| 7,771,440 | B2 | 8/2010 | Ortiz et al. |
| 7,776,060 | B2 | 8/2010 | Mooradian et al. |
| 7,793,813 | B2 | 9/2010 | Bettuchi |
| 7,802,712 | B2 | 9/2010 | Milliman et al. |
| 7,823,592 | B2 | 11/2010 | Bettuchi et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,845,536 | B2 | 12/2010 | Viola et al. |
| 7,845,538 | B2 | 12/2010 | Whitman |
| 7,857,187 | B2 | 12/2010 | Milliman |
| 7,886,951 | B2 | 2/2011 | Hessler |
| 7,896,215 | B2 | 3/2011 | Adams et al. |
| 7,900,806 | B2 | 3/2011 | Chen et al. |
| 7,909,039 | B2 | 3/2011 | Hur |
| 7,909,219 | B2 | 3/2011 | Cole et al. |
| 7,909,222 | B2 | 3/2011 | Cole et al. |
| 7,909,223 | B2 | 3/2011 | Cole et al. |
| 7,913,892 | B2 | 3/2011 | Cole et al. |
| 7,918,377 | B2 | 4/2011 | Measamer et al. |
| 7,922,062 | B2 | 4/2011 | Cole et al. |
| 7,922,743 | B2 | 4/2011 | Heinrich et al. |
| 7,931,183 | B2 | 4/2011 | Orban, III |
| 7,938,307 | B2 | 5/2011 | Bettuchi |

(56) References Cited

U.S. PATENT DOCUMENTS

| | | | |
|---|---|---|---|
| 7,942,302 | B2 | 5/2011 | Roby et al. |
| 7,951,166 | B2 | 5/2011 | Orban, III et al. |
| 7,959,050 | B2 | 6/2011 | Smith et al. |
| 7,967,181 | B2 | 6/2011 | Viola et al. |
| 7,975,895 | B2 | 7/2011 | Milliman |
| 8,002,795 | B2 | 8/2011 | Beetel |
| 8,006,701 | B2 | 8/2011 | Bilotti et al. |
| 8,006,889 | B2 | 8/2011 | Adams et al. |
| 8,011,551 | B2 | 9/2011 | Marczyk et al. |
| 8,011,554 | B2 | 9/2011 | Milliman |
| 8,012,170 | B2 | 9/2011 | Whitman et al. |
| 8,016,177 | B2 | 9/2011 | Bettuchi et al. |
| 8,016,858 | B2 | 9/2011 | Whitman |
| 8,020,741 | B2 | 9/2011 | Cole et al. |
| 8,025,199 | B2 | 9/2011 | Whitman et al. |
| 8,028,885 | B2 | 10/2011 | Smith et al. |
| 8,038,046 | B2 | 10/2011 | Smith et al. |
| 8,043,207 | B2 | 10/2011 | Adams |
| 8,066,167 | B2 | 11/2011 | Measamer et al. |
| 8,066,169 | B2 | 11/2011 | Viola |
| 8,070,035 | B2 | 12/2011 | Holsten et al. |
| 8,070,037 | B2 | 12/2011 | Csiky |
| 8,096,458 | B2 | 1/2012 | Hessler |
| 8,109,426 | B2 | 2/2012 | Milliman et al. |
| 8,109,427 | B2 | 2/2012 | Orban, III |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,123,103 | B2 | 2/2012 | Milliman |
| 8,128,645 | B2 | 3/2012 | Sonnenschein et al. |
| 8,132,703 | B2 | 3/2012 | Milliman et al. |
| 8,136,712 | B2 | 3/2012 | Zingman |
| 8,146,790 | B2 | 4/2012 | Milliman |
| 8,146,791 | B2 | 4/2012 | Bettuchi et al. |
| 8,181,838 | B2 | 5/2012 | Milliman et al. |
| 8,192,460 | B2 | 6/2012 | Orban, III et al. |
| 8,201,720 | B2 | 6/2012 | Hessler |
| 8,203,782 | B2 | 6/2012 | Brueck et al. |
| 8,210,411 | B2 | 7/2012 | Yates et al. |
| 8,211,130 | B2 | 7/2012 | Viola |
| 8,225,799 | B2 | 7/2012 | Bettuchi |
| 8,225,981 | B2 | 7/2012 | Criscuolo et al. |
| 8,231,041 | B2 | 7/2012 | Marczyk et al. |
| 8,231,042 | B2 | 7/2012 | Hessler et al. |
| 8,257,391 | B2 | 9/2012 | Orban, III et al. |
| 8,267,301 | B2 | 9/2012 | Milliman et al. |
| 8,272,552 | B2 | 9/2012 | Holsten et al. |
| 8,276,801 | B2 | 10/2012 | Zemlok et al. |
| 8,276,802 | B2 | 10/2012 | Kostrzewski |
| 8,281,975 | B2 | 10/2012 | Criscuolo et al. |
| 8,286,845 | B2 | 10/2012 | Perry et al. |
| 8,308,045 | B2 | 11/2012 | Bettuchi et al. |
| 8,312,885 | B2 | 11/2012 | Bettuchi et al. |
| 8,313,014 | B2 | 11/2012 | Bettuchi |
| 8,317,073 | B2 | 11/2012 | Milliman et al. |
| 8,317,074 | B2 | 11/2012 | Ortiz et al. |
| 8,322,590 | B2 | 12/2012 | Patel et al. |
| 8,328,060 | B2 | 12/2012 | Jankowski et al. |
| 8,328,062 | B2 | 12/2012 | Viola |
| 8,328,063 | B2 | 12/2012 | Milliman et al. |
| 8,343,185 | B2 | 1/2013 | Milliman et al. |
| 8,353,438 | B2 | 1/2013 | Baxter, III et al. |
| 8,353,439 | B2 | 1/2013 | Baxter, III et al. |
| 8,353,930 | B2 | 1/2013 | Heinrich et al. |
| 8,360,295 | B2 | 1/2013 | Milliman et al. |
| 8,365,974 | B2 | 2/2013 | Milliman |
| 8,403,942 | B2 | 3/2013 | Milliman et al. |
| 8,408,441 | B2 | 4/2013 | Wenchell et al. |
| 8,413,870 | B2 | 4/2013 | Pastorelli et al. |
| 8,413,872 | B2 | 4/2013 | Patel |
| 8,418,905 | B2 | 4/2013 | Milliman |
| 8,418,909 | B2 | 4/2013 | Kostrzewski |
| 8,424,535 | B2 | 4/2013 | Hessler et al. |
| 8,424,741 | B2 | 4/2013 | McGuckin, Jr. et al. |
| 8,430,291 | B2 | 4/2013 | Heinrich et al. |
| 8,430,292 | B2 | 4/2013 | Patel et al. |
| 8,453,910 | B2 | 6/2013 | Bettuchi et al. |
| 8,453,911 | B2 | 6/2013 | Milliman et al. |
| 8,479,968 | B2 | 7/2013 | Hodgkinson et al. |
| 8,485,414 | B2 | 7/2013 | Criscuolo et al. |
| 8,490,853 | B2 | 7/2013 | Criscuolo et al. |
| 8,511,533 | B2 | 8/2013 | Viola et al. |
| 8,551,138 | B2 | 10/2013 | Orban, III et al. |
| 8,567,655 | B2 | 10/2013 | Nalagatla et al. |
| 8,579,178 | B2 | 11/2013 | Holsten et al. |
| 8,590,763 | B2 | 11/2013 | Milliman |
| 8,590,764 | B2 | 11/2013 | Hartwick et al. |
| 8,608,047 | B2 | 12/2013 | Holsten et al. |
| 8,616,428 | B2 | 12/2013 | Milliman et al. |
| 8,616,429 | B2 | 12/2013 | Viola |
| 8,622,275 | B2 | 1/2014 | Baxter, III et al. |
| 8,627,994 | B2 | 1/2014 | Zemlok et al. |
| 8,627,995 | B2 | 1/2014 | Smith et al. |
| 8,631,993 | B2 | 1/2014 | Kostrzewski |
| 8,636,187 | B2 | 1/2014 | Hueil et al. |
| 8,640,940 | B2 | 2/2014 | Ohdaira |
| 8,646,674 | B2 | 2/2014 | Schulte et al. |
| 8,662,370 | B2 | 3/2014 | Takei |
| 8,663,258 | B2 | 3/2014 | Bettuchi et al. |
| 8,672,207 | B2 | 3/2014 | Shelton, IV et al. |
| 8,672,931 | B2 | 3/2014 | Goldboss et al. |
| 8,672,951 | B2 | 3/2014 | Smith et al. |
| 8,678,264 | B2 | 3/2014 | Racenet et al. |
| 8,679,137 | B2 | 3/2014 | Bauman et al. |
| 8,684,248 | B2 | 4/2014 | Milliman |
| 8,684,250 | B2 | 4/2014 | Bettuchi et al. |
| 8,684,251 | B2 | 4/2014 | Rebuffat et al. |
| 8,684,252 | B2 | 4/2014 | Patel et al. |
| 8,695,864 | B1 | 4/2014 | Hausen |
| 8,708,212 | B2 | 4/2014 | Williams |
| 8,733,611 | B2 | 5/2014 | Milliman |
| 8,733,615 | B2 | 5/2014 | Nalagatla et al. |
| 8,746,531 | B2 | 6/2014 | Wenchell et al. |
| 8,746,532 | B2 | 6/2014 | Nalagatla et al. |
| 8,783,543 | B2 | 7/2014 | Shelton, IV et al. |
| 8,789,737 | B2 | 7/2014 | Hodgkinson et al. |
| 8,800,838 | B2 | 8/2014 | Shelton, IV |
| 8,800,841 | B2 | 8/2014 | Ellerhorst et al. |
| 8,801,734 | B2 | 8/2014 | Shelton, IV et al. |
| 8,801,735 | B2 | 8/2014 | Shelton, IV et al. |
| 8,821,523 | B2 | 9/2014 | Heinrich et al. |
| 8,827,903 | B2 | 9/2014 | Shelton, IV et al. |
| 8,833,629 | B2 | 9/2014 | Nalagatla et al. |
| 8,840,004 | B2 | 9/2014 | Holsten et al. |
| 8,844,792 | B2 | 9/2014 | Viola |
| 8,845,661 | B2 | 9/2014 | D'Arcangelo et al. |
| 8,870,911 | B2 | 10/2014 | Williams et al. |
| 8,875,974 | B2 | 11/2014 | Rebuffat et al. |
| 8,893,948 | B2 | 11/2014 | Williams |
| 8,910,847 | B2 | 12/2014 | Nalagatla et al. |
| 8,925,785 | B2 | 1/2015 | Holsten et al. |
| 8,925,786 | B2 | 1/2015 | Holsten et al. |
| 8,967,448 | B2 | 3/2015 | Carter et al. |
| 8,978,955 | B2 | 3/2015 | Aronhalt et al. |
| 9,010,608 | B2 | 4/2015 | Casasanta et al. |
| 9,010,612 | B2 | 4/2015 | Stevenson et al. |
| 9,016,540 | B2 | 4/2015 | Whitman et al. |
| 9,237,921 | B2 | 1/2016 | Messerly et al. |
| 10,000,065 | B1 * | 6/2018 | Baker .................. B41J 2/17566 |
| 10,201,365 | B2 | 2/2019 | Boudreaux et al. |
| 10,433,848 | B2 | 10/2019 | Chen et al. |
| 10,456,134 | B2 | 10/2019 | Dinardo et al. |
| 10,463,365 | B2 | 11/2019 | Williams |
| 10,463,373 | B2 | 11/2019 | Mozdzierz et al. |
| 10,463,374 | B2 | 11/2019 | Sgroi, Jr. |
| 10,470,770 | B2 | 11/2019 | Shelton, IV et al. |
| 10,470,771 | B2 | 11/2019 | D'Agostino et al. |
| 10,499,922 | B2 | 12/2019 | Sgroi, Jr. |
| 10,506,920 | B2 | 12/2019 | Hasser et al. |
| 10,507,039 | B2 | 12/2019 | Williams |
| 10,512,467 | B2 | 12/2019 | Swayze et al. |
| 10,524,795 | B2 | 1/2020 | Nalagatla et al. |
| 10,524,798 | B2 | 1/2020 | Williams |
| 10,524,868 | B2 | 1/2020 | Cooper et al. |

(56) References Cited

U.S. PATENT DOCUMENTS

| | | | | |
|---|---|---|---|---|
| 10,537,331 | B2 | 1/2020 | Scirica et al. | |
| 10,542,993 | B2 | 1/2020 | Guerrera et al. | |
| 10,548,598 | B2 | 2/2020 | Prescott et al. | |
| 10,561,424 | B2 | 2/2020 | Penna et al. | |
| 10,568,631 | B2 | 2/2020 | Rebuffat et al. | |
| 10,575,847 | B2 | 3/2020 | Hessler et al. | |
| 10,595,871 | B2 | 3/2020 | Racenet et al. | |
| 10,595,872 | B2 | 3/2020 | Milliman | |
| 10,603,042 | B2 | 3/2020 | Sgroi | |
| 10,624,646 | B2 | 4/2020 | Bae et al. | |
| 10,639,041 | B2 | 5/2020 | Williams | |
| 10,653,414 | B2 | 5/2020 | Williams | |
| 11,045,199 | B2 * | 6/2021 | Mozdzierz | A61B 17/1155 |
| 11,109,866 | B2 * | 9/2021 | Shelton, IV | A61B 1/000096 |
| 11,190,293 | B1 * | 11/2021 | Ducellier | H04J 14/0227 |
| 11,596,400 | B2 * | 3/2023 | Mozdzierz | A61B 17/068 |
| 11,911,038 | B2 * | 2/2024 | Joyce | A61B 17/1155 |
| 2001/0022564 | A1 * | 9/2001 | Youngquist | G09F 9/33 345/55 |
| 2001/0043297 | A1 * | 11/2001 | Arai | G02F 1/133504 349/114 |
| 2003/0111507 | A1 | 6/2003 | Nunez | |
| 2004/0092992 | A1 * | 5/2004 | Adams | A61B 17/26 606/180 |
| 2005/0051597 | A1 | 3/2005 | Toledano | |
| 2005/0107813 | A1 | 5/2005 | Gilete Garcia | |
| 2006/0000869 | A1 | 1/2006 | Fontayne | |
| 2006/0011698 | A1 | 1/2006 | Okada et al. | |
| 2006/0201989 | A1 | 9/2006 | Ojeda | |
| 2007/0027473 | A1 | 2/2007 | Vresh et al. | |
| 2007/0029363 | A1 | 2/2007 | Popov | |
| 2007/0060952 | A1 | 3/2007 | Roby et al. | |
| 2008/0245841 | A1 | 10/2008 | Smith et al. | |
| 2008/0251568 | A1 | 10/2008 | Zemlok et al. | |
| 2009/0236392 | A1 | 9/2009 | Cole et al. | |
| 2009/0236398 | A1 | 9/2009 | Cole et al. | |
| 2009/0236401 | A1 | 9/2009 | Cole et al. | |
| 2010/0019016 | A1 | 1/2010 | Edoga et al. | |
| 2010/0051668 | A1 | 3/2010 | Milliman et al. | |
| 2010/0069942 | A1 | 3/2010 | Shelton, IV | |
| 2010/0084453 | A1 | 4/2010 | Hu | |
| 2010/0096431 | A1 | 4/2010 | Smith et al. | |
| 2010/0147923 | A1 | 6/2010 | D'Agostino et al. | |
| 2010/0163598 | A1 | 7/2010 | Belzer | |
| 2010/0224668 | A1 | 9/2010 | Fontayne et al. | |
| 2010/0230465 | A1 | 9/2010 | Smith et al. | |
| 2010/0258611 | A1 | 10/2010 | Smith et al. | |
| 2010/0264195 | A1 | 10/2010 | Bettuchi | |
| 2010/0270355 | A1 | 10/2010 | Whitman et al. | |
| 2010/0327041 | A1 | 12/2010 | Milliman et al. | |
| 2011/0011916 | A1 | 1/2011 | Levine | |
| 2011/0114697 | A1 | 5/2011 | Baxter, III et al. | |
| 2011/0114700 | A1 | 5/2011 | Baxter, III et al. | |
| 2011/0139851 | A1 | 6/2011 | McCuen | |
| 2011/0144640 | A1 | 6/2011 | Heinrich et al. | |
| 2011/0155781 | A1 | 6/2011 | Swensgard et al. | |
| 2011/0192882 | A1 | 8/2011 | Hess et al. | |
| 2011/0204119 | A1 | 8/2011 | McCuen | |
| 2011/0270355 | A1 | 11/2011 | Chambers | |
| 2011/0288573 | A1 | 11/2011 | Yates et al. | |
| 2012/0145755 | A1 | 6/2012 | Kahn | |
| 2012/0193395 | A1 | 8/2012 | Pastorelli et al. | |
| 2012/0193398 | A1 | 8/2012 | Williams et al. | |
| 2012/0232339 | A1 | 9/2012 | Csiky | |
| 2012/0273548 | A1 | 11/2012 | Ma et al. | |
| 2012/0325888 | A1 | 12/2012 | Qiao et al. | |
| 2013/0015232 | A1 | 1/2013 | Smith et al. | |
| 2013/0020372 | A1 | 1/2013 | Jankowski et al. | |
| 2013/0020373 | A1 | 1/2013 | Smith et al. | |
| 2013/0032628 | A1 | 2/2013 | Li et al. | |
| 2013/0060258 | A1 | 3/2013 | Giacomantonio | |
| 2013/0105544 | A1 | 5/2013 | Mozdzierz et al. | |
| 2013/0105546 | A1 | 5/2013 | Milliman et al. | |
| 2013/0105551 | A1 | 5/2013 | Zingman | |
| 2013/0126580 | A1 | 5/2013 | Smith et al. | |
| 2013/0153630 | A1 | 6/2013 | Miller et al. | |
| 2013/0153631 | A1 | 6/2013 | Vasudevan et al. | |
| 2013/0153638 | A1 | 6/2013 | Carter et al. | |
| 2013/0153639 | A1 | 6/2013 | Hodgkinson et al. | |
| 2013/0175315 | A1 | 7/2013 | Milliman | |
| 2013/0175318 | A1 | 7/2013 | Felder et al. | |
| 2013/0175319 | A1 | 7/2013 | Felder et al. | |
| 2013/0175320 | A1 | 7/2013 | Mandakolathur Vasudevan et al. | |
| 2013/0181035 | A1 | 7/2013 | Milliman | |
| 2013/0181036 | A1 | 7/2013 | Olson et al. | |
| 2013/0193185 | A1 | 8/2013 | Patel | |
| 2013/0193187 | A1 | 8/2013 | Milliman | |
| 2013/0193190 | A1 | 8/2013 | Carter et al. | |
| 2013/0193192 | A1 | 8/2013 | Casasanta, Jr. et al. | |
| 2013/0200131 | A1 | 8/2013 | Racenet et al. | |
| 2013/0206816 | A1 | 8/2013 | Penna | |
| 2013/0214027 | A1 | 8/2013 | Hessler et al. | |
| 2013/0214028 | A1 | 8/2013 | Patel et al. | |
| 2013/0228609 | A1 | 9/2013 | Kostrzewski | |
| 2013/0240597 | A1 | 9/2013 | Milliman et al. | |
| 2013/0240600 | A1 | 9/2013 | Bettuchi | |
| 2013/0248581 | A1 | 9/2013 | Smith et al. | |
| 2013/0277411 | A1 | 10/2013 | Hodgkinson et al. | |
| 2013/0277412 | A1 | 10/2013 | Gresham et al. | |
| 2013/0284792 | A1 | 10/2013 | Ma | |
| 2013/0292449 | A1 | 11/2013 | Bettuchi et al. | |
| 2013/0299553 | A1 | 11/2013 | Mozdzierz | |
| 2013/0299554 | A1 | 11/2013 | Mozdzierz | |
| 2013/0306701 | A1 | 11/2013 | Olson | |
| 2013/0306707 | A1 | 11/2013 | Viola et al. | |
| 2014/0008413 | A1 | 1/2014 | Williams | |
| 2014/0012317 | A1 | 1/2014 | Orban et al. | |
| 2014/0046352 | A1 | 2/2014 | Reboa et al. | |
| 2014/0158747 | A1 | 6/2014 | Measamer et al. | |
| 2014/0246474 | A1 * | 9/2014 | Hall | A61B 17/320092 227/175.1 |
| 2014/0284370 | A1 | 9/2014 | Sahin | |
| 2015/0053749 | A1 | 2/2015 | Shelton, IV et al. | |
| 2015/0083772 | A1 | 3/2015 | Miller et al. | |
| 2015/0173763 | A1 | 6/2015 | Liu | |
| 2015/0209045 | A1 | 7/2015 | Hodgkinson et al. | |
| 2015/0282825 | A1 * | 10/2015 | Trees | A61B 18/1445 606/170 |
| 2016/0066916 | A1 * | 3/2016 | Overmyer | A61B 17/07207 227/176.1 |
| 2016/0143641 | A1 | 5/2016 | Sapienza et al. | |
| 2016/0157856 | A1 | 6/2016 | Williams et al. | |
| 2016/0302792 | A1 | 10/2016 | Motai | |
| 2017/0128068 | A1 | 5/2017 | Zhang et al. | |
| 2017/0296185 | A1 * | 10/2017 | Swensgard | A61B 17/068 |
| 2017/0333033 | A1 | 11/2017 | Valentine et al. | |
| 2018/0353186 | A1 * | 12/2018 | Mozdzierz | A61B 17/1155 |
| 2018/0360446 | A1 * | 12/2018 | Shelton, IV | A61B 17/068 |
| 2019/0099180 | A1 * | 4/2019 | Leimbach | G16H 20/40 |
| 2019/0200998 | A1 | 7/2019 | Shelton, IV et al. | |
| 2019/0201034 | A1 * | 7/2019 | Shelton, IV | A61B 17/068 |
| 2019/0314015 | A1 * | 10/2019 | Shelton, IV | A61B 90/03 |
| 2020/0155149 | A1 * | 5/2020 | Calderoni | H01H 13/50 |
| 2020/0405304 | A1 * | 12/2020 | Mozdzierz | A61B 17/068 |
| 2022/0060802 | A1 * | 2/2022 | Richter | G06V 20/20 |
| 2024/0188960 | A1 | 6/2024 | Joyce et al. | |

FOREIGN PATENT DOCUMENTS

| | | | |
|---|---|---|---|
| CN | 104039244 | A | 9/2014 |
| CN | 104042288 | A | 9/2014 |
| CN | 104367360 | A | 2/2015 |
| DE | 1057729 | B | 5/1959 |
| DE | 3301713 | A1 | 7/1984 |
| EP | 0152382 | A2 | 8/1985 |
| EP | 0173451 | A1 | 3/1986 |
| EP | 0190022 | A2 | 8/1986 |
| EP | 0282157 | A1 | 9/1988 |
| EP | 0503689 | A2 | 9/1992 |
| EP | 1354560 | A2 | 10/2003 |
| EP | 2138118 | A2 | 12/2009 |
| EP | 2168510 | A1 | 3/2010 |
| EP | 2238926 | A2 | 10/2010 |
| EP | 2524656 | A2 | 11/2012 |

(56) References Cited

FOREIGN PATENT DOCUMENTS

| | | | |
|---|---|---|---|
| EP | 3231373 | A2 | 10/2017 |
| EP | 3417804 | A1 | 12/2018 |
| EP | 3420972 | A1 | 1/2019 |
| FR | 1136020 | A | 5/1957 |
| FR | 1461464 | A | 2/1966 |
| FR | 1588250 | A | 4/1970 |
| FR | 2443239 | A1 | 7/1980 |
| GB | 1185292 | A | 3/1970 |
| GB | 2016991 | A | 10/1979 |
| GB | 2070499 | A | 9/1981 |
| JP | 2004147969 | A | 5/2004 |
| JP | 2013138860 | A | 7/2013 |
| NL | 7711347 | A | 4/1979 |
| SU | 1509052 | A1 | 9/1989 |
| WO | 8706448 | A1 | 11/1987 |
| WO | 8900406 | A1 | 1/1989 |
| WO | 9006085 | A1 | 6/1990 |
| WO | 9835614 | A1 | 8/1998 |
| WO | 0154594 | A1 | 8/2001 |
| WO | 02080781 | A2 | 10/2002 |
| WO | 2008107918 | A1 | 9/2008 |

OTHER PUBLICATIONS

Extended European Search Report received for European Patent Application No. 14181908.6, mailed on May 26, 2015, 10 pages.

Extended European Search Report received for European Patent Application No. 21151140.7, mailed on Mar. 17, 2021, 9 pages.

Notice of Allowance received for U.S. Appl. No. 18/585,215, mailed on Mar. 19, 2025, 9 pages.

Office Action received for European Patent Application No. 14181908.6, mailed on May 3, 2016, 5 pages.

* cited by examiner

CUT OPTIMIZATION FOR EXCESSIVE TISSUE CONDITIONS

CROSS-REFERENCE TO RELATED APPLICATIONS

This application is a continuation of U.S. patent application Ser. No. 18/585,215 filed on Feb. 23, 2024, which is a continuation of U.S. patent application Ser. No. 17/120,659 filed on Dec. 14, 2020, now U.S. Pat. No. 11,911,038, which claims the benefit of and priority to U.S. Provisional Patent Application Ser. No. 62/960,202 filed on Jan. 13, 2020, the entire disclosures of which are incorporated by reference herein.

FIELD

The disclosure is directed to powered circular stapling devices and, more particularly, to optimizing the cutting stroke of powered circular stapling devices.

BACKGROUND

Conventional powered circular stapling devices typically include a one-time use circular reload releasably secured to a reusable adapter and/or a handle assembly. During a stapling procedure, two layers of tissue are clamped between the circular reload and an anvil assembly that is attached to a trocar of the adapter assembly. After the tissue is clamped between the circular reload and the anvil assembly to define a specific tissue gap between the circular reload and the anvil assembly, the handle assembly can be actuated to drive a staple pusher within the circular reload and advance staples through the tissue into staple pockets on the anvil assembly.

Subsequent to staple formation, the handle assembly can be actuated to drive a knife pusher within the circular reload at a steady speed to advance an annular knife from within the circular reload. As the annular knife is advanced, the annular knife engages and cuts a hole in the clamped and stapled tissue to form an anastomosis. The knife pusher is then retracted, returning the annular knife back into the circular reload to prevent exposure of the annular knife. The knife pusher may retract the annular knife beyond its initial position to, for example, engage detents which retain the annular knife within the circular reload.

Prior to advancing the knife pusher, a large amount of tissue may be captured within the circular reload and/or between the circular reload and the anvil assembly. Current software controls the annular knife by moving the knife pusher at a constant speed until a specified cut force limit, e.g., 275 lbf, is detected by a strain gage supported inside the handle assembly or adapter assembly. Excessive amounts of tissue inside the circular reload and/or between the circular reload and the anvil assembly during advancement of the knife assembly may raise the amount of pressure against the knife pusher assembly such that the cut force limit is reached prior to the annular knife completely cutting through the tissue. This may result in an incomplete cut.

Therefore, it would be beneficial to have a powered circular stapling device with an optimized cutting stroke for accommodating a large amount of tissue inside the circular reload.

SUMMARY

A method of operating a surgical stapler is provided. The method includes advancing a knife assembly at a first velocity until a predetermined force on the knife assembly is detected, advancing the knife assembly at a second velocity when the predetermined force is detected, the second velocity being less than the first velocity, and continuing to advance the knife assembly at the second velocity until the knife assembly travels a cutting stroke distance.

In embodiments, the first velocity is from about 3.5 in/min to about 4.0 in/min. The second velocity may be from about 0.25 in/min to about 0.5 in/min. The predetermined force may be about 275 lbf. The cutting stroke distance may be from about 0.20 in. to about 0.350 in. The cutting stroke distance may be about 0.325 in.

Another method of operating a surgical stapler is provided including advancing a knife assembly at a first velocity until a predetermined force on the knife assembly is detected, advancing the knife assembly at a second velocity when the predetermined force is detected, the second velocity being less than the first velocity, continuing to advance the knife assembly at the second velocity until a second predetermined force on the knife assembly is detected, and advancing the knife assembly at a third velocity until the knife assembly travels a cutting stroke distance.

In embodiments, the first velocity is from about 3.5 in/min to about 4.0 in/min. The second velocity may be from about 0.25 in/min to about 0.5 in/min. The predetermined force may be about 275 lbf. The cutting stroke distance may be from about 0.20 in. to about 0.350 in. The cutting stroke distance may be about 0.325 in.

BRIEF DESCRIPTION OF THE DRAWINGS

Various aspects of the disclosed circular reload are described herein below with reference to the drawings, wherein.

DETAILED DESCRIPTION

Figure 1:
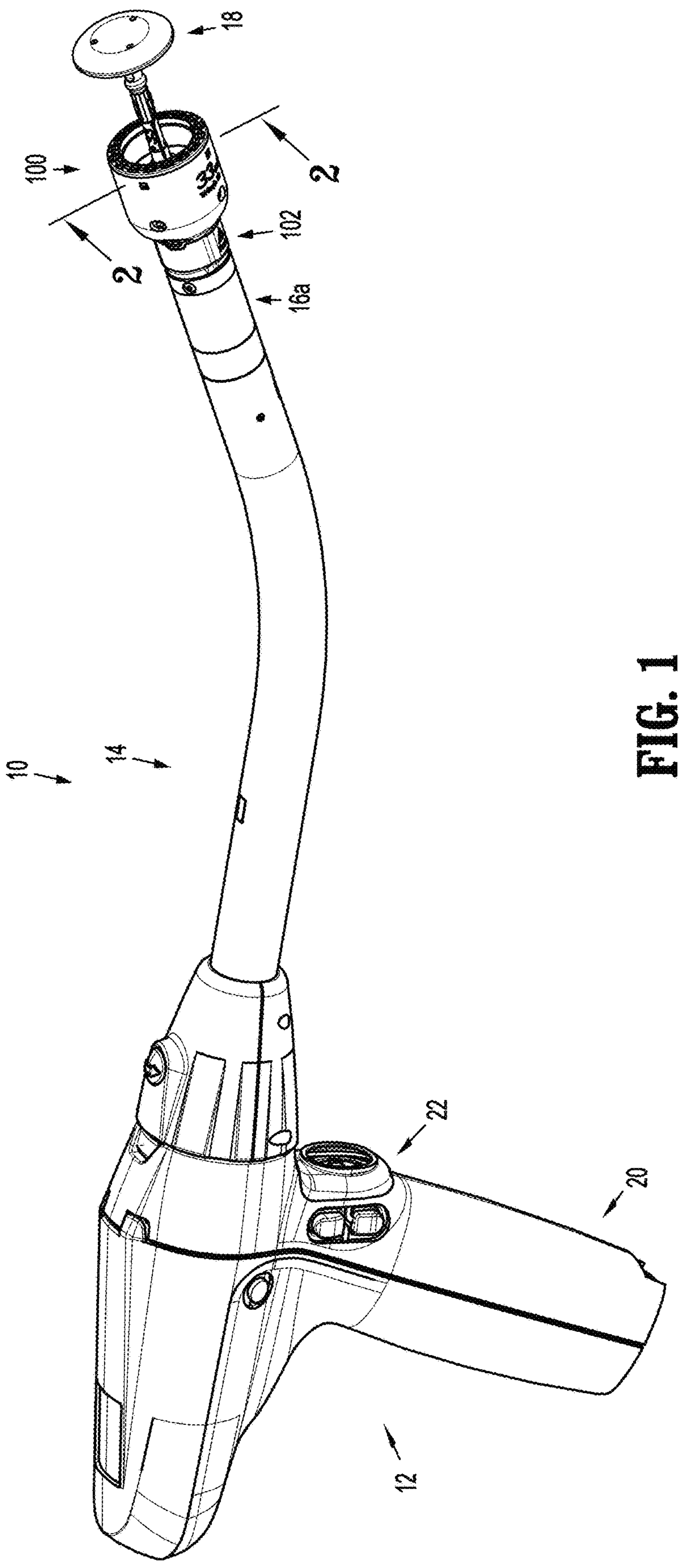
FIG. 1 is a side perspective view of a circular stapling device including exemplary aspects of the disclosed circular reload in accordance with the disclosure.

The disclosed circular reload will now be described in detail with reference to the drawings in which like reference numerals designate identical or corresponding elements in each of the several views. However, it is to be understood that the aspects of the disclosure provided herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term “proximal” is used generally to refer to that portion of the device that is closer to a clinician, while the term “distal” is used generally to refer to that portion of the device that is farther from the clinician. In addition, the term “endoscopic” is used generally used to refer to endoscopic, laparoscopic, arthroscopic, and/or any other procedure conducted through small diameter incision or cannula. Further, the term “clinician” is used generally to refer to medical personnel including doctors, nurses, and support personnel. As used herein, the term "about" means that the numerical value is approximate and small variations would not significantly affect the practice of the disclosed embodiments. Where a numerical limitation is used, unless indicated otherwise by the context, "about" means the numerical value can vary by +10% and remain within the scope of the disclosed embodiments.

Figure 2:
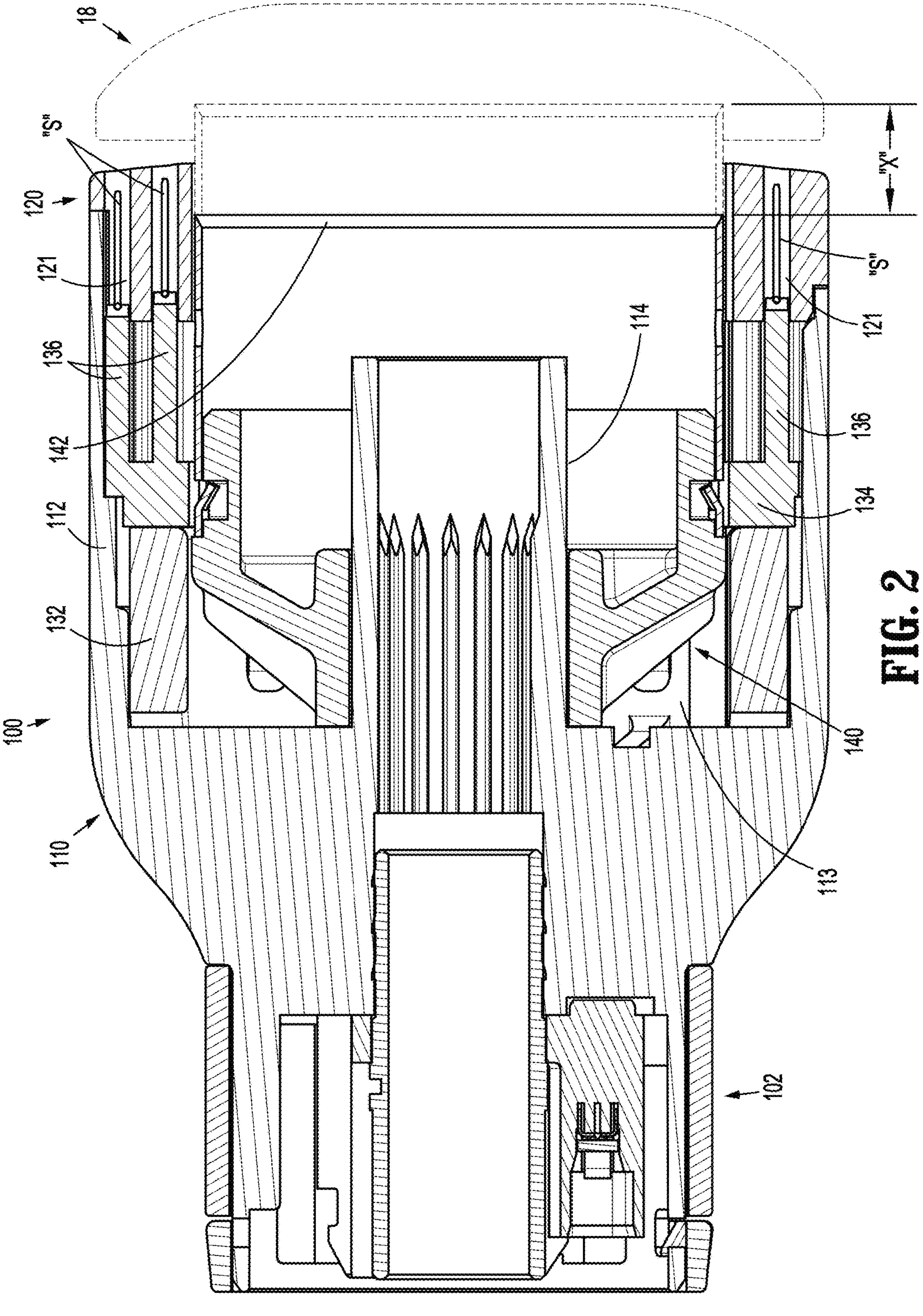
FIG. 2 is a side perspective view of the circular reload of FIG. 1.

FIGS. 1 and 2 illustrate a circular stapling device 10 including an exemplary circular reload shown generally as circular reload 100. The stapling device 10 includes a handle assembly 12, an elongate body or adaptor assembly 14, the circular reload 100, and an anvil assembly 18 that is supported for movement in relation to the circular reload 100 between spaced and approximated or clamped positions as is known in the art. The circular reload 100 includes a proximal portion 102 that is releasably coupled to a distal portion 16*a* of the elongate body 16. The handle assembly 12 includes a stationary grip 20 that supports actuation buttons 22 for controlling operation of various functions of the stapling device 10 including approximation of the circular reload 100 and anvil assembly 18, firing of staples from the circular reload 100, and cutting or coring of tissue (not shown) clamped between the circular reload 100 and the anvil assembly 18.

The stapling device 10 is illustrated as an electrically powered stapling device including an electrically powered handle assembly 12 that may support one or more batteries (not shown). The elongate body 14 is in the form of an adaptor assembly 14 that translates power from the handle assembly 12 to the circular reload 100 and anvil assembly 18. Examples of electrically powered stapling devices can be found in U.S. Pat. Nos. 9,055,943, 9,023,014, and U.S. Publication Nos. 2018/0125495 ("the '495 Publication"), and 2017/0340351.

FIG. 2 illustrates the circular reload 100 which includes a shell housing 110, a staple cartridge 120 supporting a plurality of staples "S", a staple pusher assembly 130, and a knife pusher assembly 140 that supports an annular knife 132. The staple cartridge 120 is annular and defines annular rows of staple pockets 121. Each of the staple pockets 121 supports one of the plurality of staples "S". The circular reload 100 will only be described in detail to the extent necessary to fully disclose the novel aspects of the disclosure. For a detailed description of an exemplary circular reload, please refer to the '495 Publication.

Briefly, the staple pusher assembly 130 of the circular reload 100 includes a staple pushing member 132 and an annular pusher 134. The annular pusher 134 of the circular reload 100 has a plurality of fingers 136. Each of the plurality of fingers 136 is received within a respective one of the staple pockets 121 of the staple cartridge 120 and is movable through the respective staple pocket 121 to eject the staples "S" from the staple pockets 121 when the staple pushing member 132 is moved from a retracted position to an advanced position within the shell housing 110.

The shell housing 110 of the circular reload 100 includes an outer housing portion 112 and an inner housing portion 114 spaced from the outer housing portion 112 to define an annular cavity 113. The pusher assembly 130 is movable within the annular cavity 113 between a retracted position (FIG. 2) and an advanced position (not shown) independently of the knife pusher assembly 140 to eject the staples "S" from the staple cartridge 120. The knife pusher assembly 140, including the annular knife 142, is movable from a retracted position (FIG. 2) to an advanced position (shown in phantom) to cut the tissue (not shown).

The distance between the position of the annular knife 142 when the knife pusher assembly 140 is in the retracted position and the position of the annular knife 142 when the knife pusher assembly 140 is in the advanced position is indicated in FIG. 2 as a cutting stroke distance "X". In embodiments, the cutting stroke distance "X" is from about 0.20 inches to about 0.35 inches. In certain embodiments, the cutting stroke distance "X" is about 0.325 inches. To ensure that the tissue (not shown) clamped between the circular reload 100 and the anvil assembly 18 is completely cut during a stapling procedure, it is necessary for the annular knife 142 to travel the entire cutting stroke distance "X".

To prevent damage to the components of the circular stapling device 10 during a stapling procedure, the force applied to knife pusher assembly 140 is typically limited to a predetermined force. For example, in certain aspects of the disclosure, the cut force limit is 275 lbf. However, during the stapling procedure, an excessive amount of tissue (not shown) may become trapped within the circular reload 100 and/or between the circular reload 100 and the anvil assembly 18 and may cause the cut force limit of the circular stapling device 10 to be reached before the annular knife 142 travels the entire cutting stroke distance "X". This may result in an incomplete cut of the tissue.

In order to compensate for excessive amounts of tissue that may be clamped between the circular reload 100 and the anvil assembly 18, software included with the circular stapling device 10 is programmed to reduce a speed of travel, i.e., velocity, of the knife pusher assembly 140, and more particularly, the annular knife 142, when the cut force limit is reached prior to the annular knife 142 travelling through the entire cutting stroke distance "X". The software may also increase the cut force limit. In aspects of the disclosure, the velocity of the annular knife 142 is reduced by 10%. In embodiments, a first or initial velocity of the knife pusher assembly 140 is from about 3.5 in/min to about 4.0 in/min. and a second velocity is from about 0.25 in/min to about 0.5 in/min. Simultaneously, the cut force limit may be increased to, for example, 350 lbf. By reducing the speed at which the annular knife 142 travels, the excess tissue trapped within the circular reload 100 and/or between the circular reload 100 and the anvil assembly 18 is able to relax, i.e., release fluid, and return to a state of equilibrium.

In instances where the initial velocity of the annular knife 142 is reduced to the second velocity and the increased cut force limit is attained before the annular knife 142 travels the entire cutting stroke distance "X", the velocity of the annular knife 142 may be further reduced to a third velocity. The further reduction in velocity may also be accompanied by an increase in the cut force limit. Subsequent reductions in velocity of the annular knife 142 and increases in the cut force limit may occur until the annular knife 142 travels the entire cutting stroke distance "X".

Figure 3:
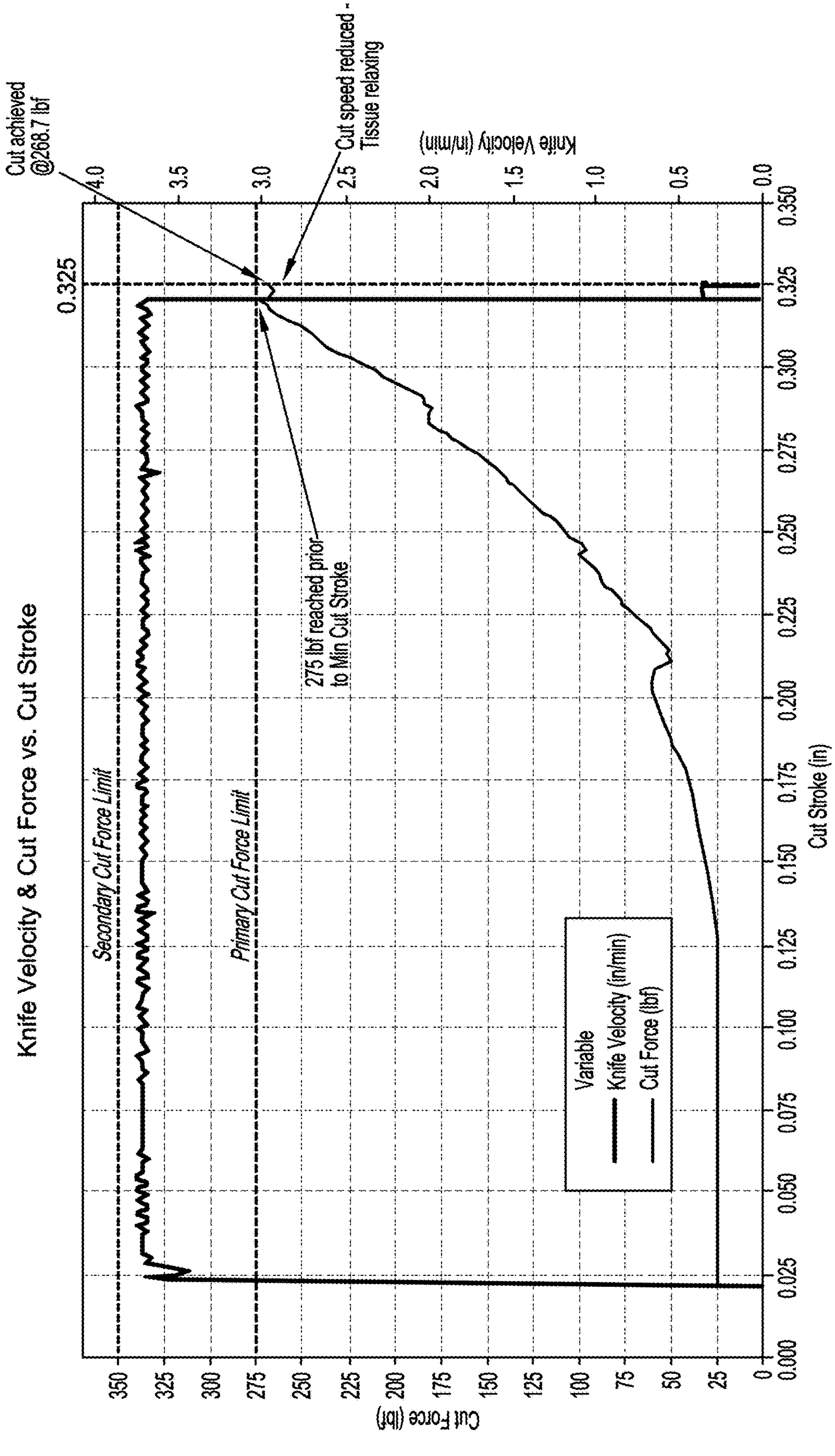
FIG. 3 is a chart plotting knife velocity and cut force relative to cut stroke.

As illustrated in the chart of FIG. 3, by reducing the speed of the annular knife 142 to allow time for the tissue clamped within the circular reload 100 to relax, the cut force required to move the annular knife 142 through the entire cut stroke distance "X" is reduced.

In other aspects of the disclosure, the annular knife 142 may be moved at an initial velocity until the annular knife 142 experiences resistance, i.e., the annular knife 142 engages tissue. The velocity of the annular knife 142 may then be reduced, as described above, until the annular knife 142 travels the entire cutting stroke distance "X". Increasing the velocity of the annular knife 142 prior to the annular knife 142 engaging tissue reduces firing time of the surgical stapling device 10 when the annular knife 142 travels through the circular reload 100.

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A powered stapling device, comprising:

a staple cartridge including a plurality of staples and a knife pusher assembly, the knife pusher assembly having a knife for advancement in a distal direction for cutting tissue;

a sensor configured to sense a cutting force on the knife;

an anvil assembly movable relative to the staple cartridge; and software configured to:

advance the knife pusher assembly at a first speed;

during advancement at the first speed, detect that the cutting force meets or exceeds a first force threshold;

based on the cutting force meeting or exceeding the first force threshold, advance the knife pusher assembly at a second speed less than the first speed;

during advancement at the second speed, detect that the cutting force meets or exceeds a second force threshold greater than the first force threshold, while a travel distance of the knife pusher assembly is less than a minimum distance threshold; and advance the knife pusher assembly at a third speed less than the second speed, based on the cutting force meeting or exceeding the second force threshold while the travel distance is less than the minimum distance threshold.

2. The powered stapling device of claim 1, wherein the first force threshold corresponds to initial tissue engagement by the knife.

3. The powered stapling device of claim 2, wherein the second force threshold is about 275 lbf.

4. The powered stapling device of claim 1, wherein the software is further configured to:

during advancement at the third speed, detect that the cutting force meets or exceeds a third force threshold greater than the second force threshold, while the travel distance is less than the minimum distance threshold; and advance the knife pusher assembly at a fourth speed less than the third speed, based on the cutting force meeting or exceeding the third force threshold while the travel distance is less than the minimum distance threshold.

5. The powered stapling device of claim 4, wherein the third force threshold is about 350 lbf.

6. The powered stapling device of claim 1, wherein the software is further configured to:

determine that the knife has made a complete cut through the tissue; and stop advancement of the knife pusher assembly.

7. The powered stapling device of claim 6, wherein determining that the knife has made the complete cut comprises detecting that the cutting force meets or exceeds the second force threshold while the travel distance meets or exceeds the minimum distance threshold.

8. The powered stapling device of claim 1, wherein the software is further configured to:

determine that the knife has made an incomplete cut through the tissue; and stop advancement of the knife pusher assembly.

9. The powered stapling device of claim 8, wherein determining that the knife has made the incomplete cut comprises detecting that that the cutting force meets or exceeds a maximum force threshold while the travel distance meets or exceeds a maximum distance threshold greater than the minimum distance threshold.

10. The powered stapling device of claim 9, wherein the maximum force threshold is about 350 lbf.

11. The powered stapling device of claim 1, wherein the knife comprises an annular knife, and the staple cartridge defines annular rows of staple pockets.

12. A method performed by a surgical stapler, the method comprising:

advancing a knife pusher assembly while sensing a cutting force on a knife of the knife pusher assembly;

during advancement at a first speed, detecting that the cutting force meets or exceeds a first force threshold;

based on the cutting force meeting or exceeding the first force threshold, advancing the knife pusher assembly at a second speed less than the first speed; and during advancement at the second speed, detecting that the cutting force meets or exceeds a second force threshold greater than the first force threshold, while a travel distance of the knife pusher assembly is less than a minimum distance threshold; and advancing the knife pusher assembly at a third speed less than the second speed.

13. The method of claim 12, further comprising:

during advancement at the third speed, detecting that the cutting force meets or exceeds a third force threshold greater than the second force threshold, while the travel distance is less than the minimum distance threshold; and advancing the knife pusher assembly at a fourth speed less than the third speed.

14. The method of claim 12, further comprising determining that the knife has made a complete cut through tissue by detecting that the cutting force meets or exceeds the second force threshold while the travel distance meets or exceeds the minimum distance threshold.

* * * * *